(12) United States Patent
Bernhard et al.

(10) Patent No.: US 9,395,381 B2
(45) Date of Patent: Jul. 19, 2016

(54) DEVICE FOR TRANSPORTING REACTION VESSELS

(71) Applicant: Siemens Healthcare Diagnostics Products GmbH, Marburg (DE)

(72) Inventors: Joachim Bernhard, Karben (DE); Joerg Filzinger, Kriftel (DE); Hugo Wilmes, Ban Soden (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 155 days.

(21) Appl. No.: 14/151,393

(22) Filed: Jan. 9, 2014

(65) Prior Publication Data

US 2014/0193300 A1    Jul. 10, 2014

(30) Foreign Application Priority Data

Jan. 9, 2013 (EP) .................................... 13150593

(51) Int. Cl.
*G01N 35/02* (2006.01)
*G01N 35/04* (2006.01)
*B01L 9/00* (2006.01)

(52) U.S. Cl.
CPC .............. *G01N 35/025* (2013.01); *G01N 35/04* (2013.01); *B01L 9/00* (2013.01); *B01L 2200/16* (2013.01); *G01N 2035/0439* (2013.01); *G01N 2035/0444* (2013.01); *G01N 2035/0451* (2013.01)

(58) Field of Classification Search
None
See application file for complete search history.

(56) References Cited

U.S. PATENT DOCUMENTS

| 5,582,796 | A  | * | 12/1996 | Carey et al. ...................... 422/65 |
| 2001/0019826 | A1 | * | 9/2001 | Ammann .......................... 435/6 |
| 2003/0215365 | A1 |  | 11/2003 | Sevigny et al. |
| 2004/0020310 | A1 |  | 2/2004 | Escal |
| 2005/0169801 | A1 | * | 8/2005 | Fogel .................... B01L 9/06 422/64 |
| 2006/0263248 | A1 | * | 11/2006 | Gomm et al. ................... 422/63 |
| 2007/0065945 | A1 |  | 3/2007 | Sigrist |
| 2007/0104614 | A1 | * | 5/2007 | Wang ............... G01N 35/00594 422/64 |
| 2007/0134135 | A1 |  | 6/2007 | Li et al. |
| 2007/0229830 | A1 | * | 10/2007 | Yamamoto et al. ........... 356/414 |
| 2008/0095666 | A1 | * | 4/2008 | Burkhardt et al. .............. 422/64 |
| 2008/0190735 | A1 | * | 8/2008 | Luoma ..................... B01L 9/00 198/340 |

FOREIGN PATENT DOCUMENTS

| EP | 0369840 A1 | 5/1990 |
| WO | 94/14073 A1 | 6/1994 |

OTHER PUBLICATIONS

European Search Report and Written Opinion of European patent Application No. 13150593.5 dated Oct. 23, 2013 (8 Pages).
European Search Report of European patent Application No. 13197586.4 dated May 13, 2014 (5 Pages).

* cited by examiner

*Primary Examiner* — Jill Warden
*Assistant Examiner* — Benjamin Whatley
(74) *Attorney, Agent, or Firm* — Dugan & Dugan, PC

(57) ABSTRACT

The invention relates to a rotatable device (1) for transporting reaction vessels in an automatic analysis apparatus, said device (1) comprising a circular base plate (16), and a number of holders (2) which are connected to the base plate (16), are preferably made of a plastic and comprise the receiving positions (4, 6) for the reaction vessels.

14 Claims, 5 Drawing Sheets

Figure 3:
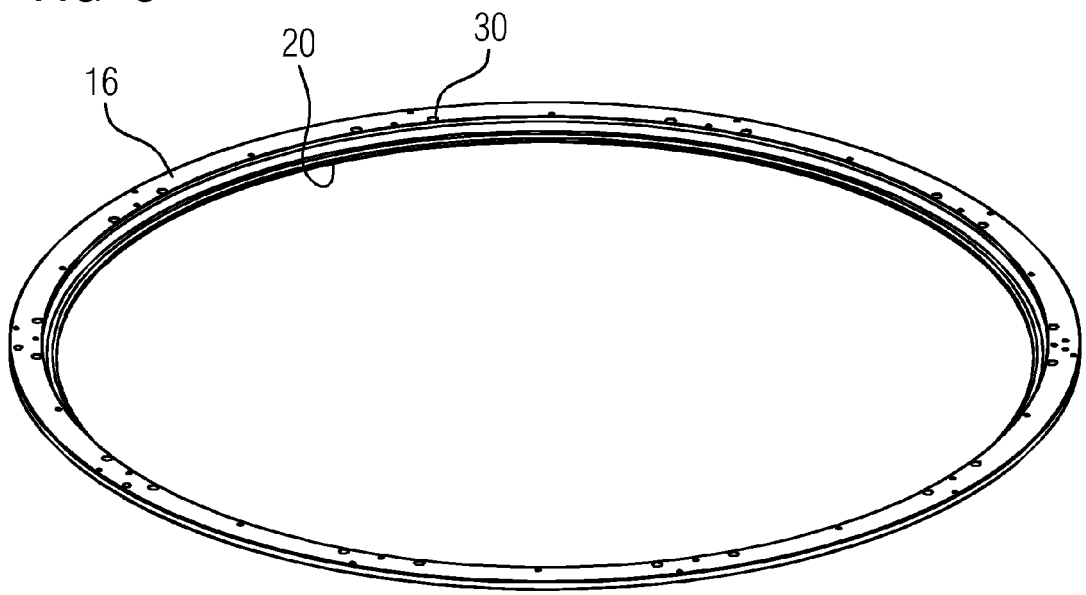

FIG 1
FIG 2
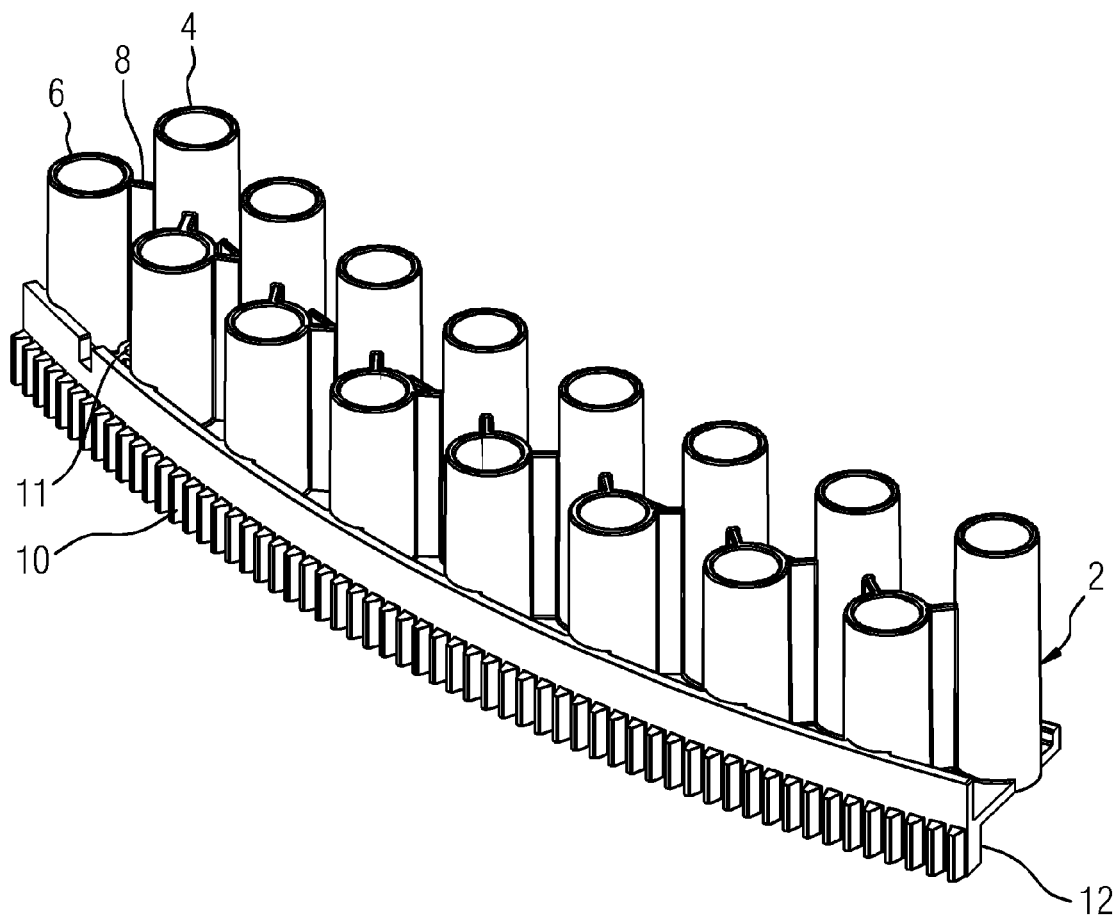
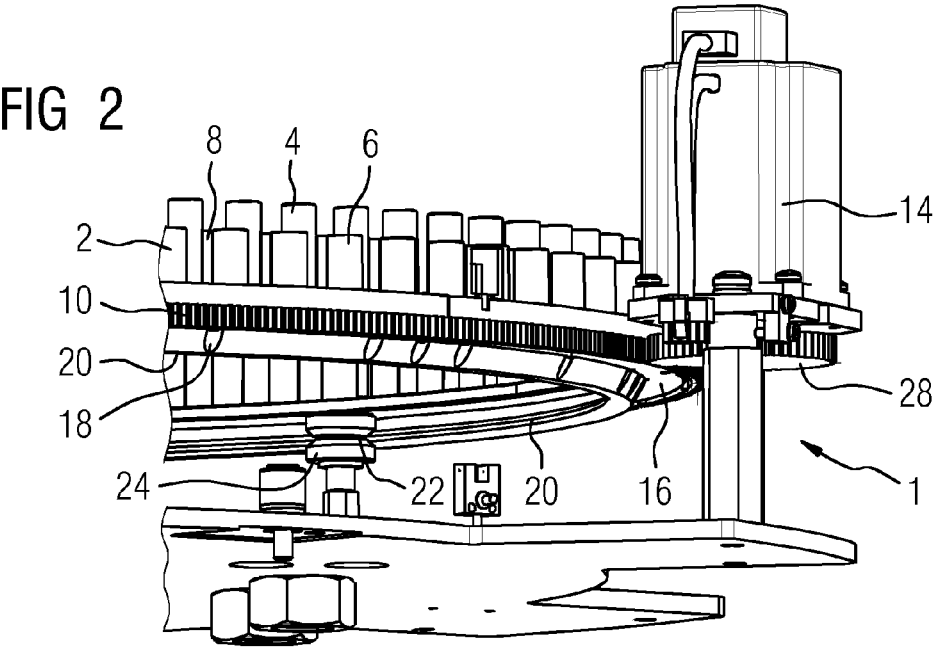

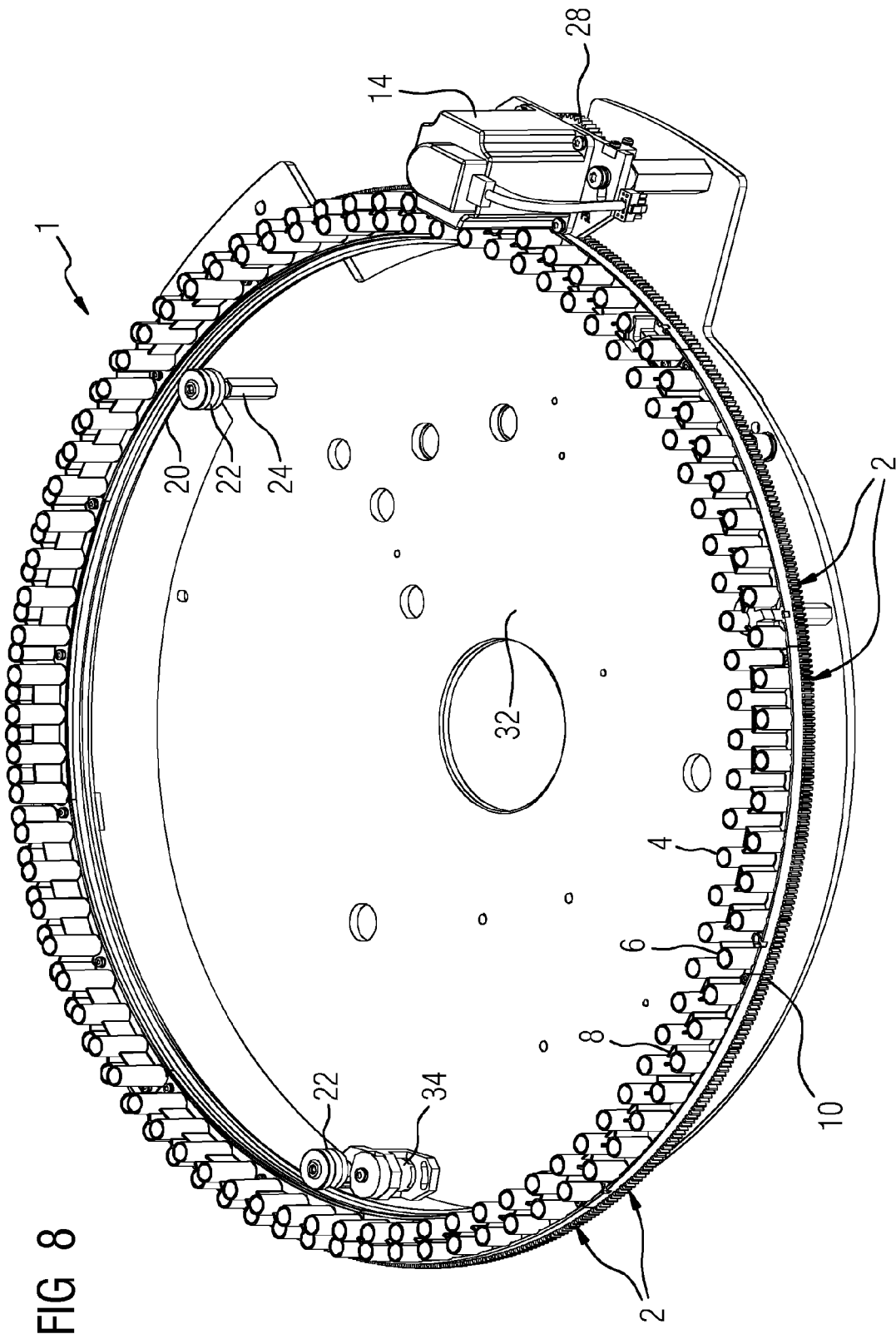

DEVICE FOR TRANSPORTING REACTION VESSELS

The invention relates to a device for transporting reaction vessels in an automatic analysis apparatus, said device comprising a circular base plate, and a plurality of circular-ring-segment-shaped holders which are connected releasably to the base plate and are provided for reaction vessels.

Numerous detection and analysis methods for determining physiological parameters in samples of bodily fluid such as blood, plasma, serum or urine or in other biological samples are carried out in an automated manner in corresponding analysis apparatus.

Current analysis apparatus are able to carry out many different kinds of detection reactions and analyses with a large number of samples. Analysis apparatus of the kind presently used in clinical laboratories or in blood banks usually comprise an area for the delivery of sample vessels that contain the primary samples to be analyzed. To feed the sample vessels into the analysis apparatus, a transport system is usually provided which firstly transports the sample vessels to a sample identification device, which detects sample-specific information applied to a sample vessel and transmits said information to a storage unit. Thereafter, the sample vessels are transported to a sampling station. With the aid of a sample pipetting device, at least one aliquot of the sample liquid is removed there from a sample vessel and is transferred to a reaction vessel.

The reaction vessels are generally in the form of disposable cuvettes which are stored in a cuvette container in the analysis apparatus and which are transferred automatically from the storage container to defined receiving positions. However, there are also apparatus in which the cuvettes are re-used, by being washed before the next use. The reagents needed for providing different types of test-specific reaction mixtures are located in reagent containers, which are stored in a reagent station. The reagent containers are delivered to the analysis apparatus either automatically or manually.

Measurement systems which are based on photometric (e.g. turbidimetric, nephelometric, fluorometric or luminometric) or radiometric measurement principles are particularly common. These methods permit the qualitative and quantitative detection of analytes in liquid samples, without having to provide additional separating steps. Clinically relevant parameters, such as the concentration or the activity of an analyte, are often determined by virtue of an aliquot of a bodily fluid of a patient being mixed, simultaneously or in succession, with one or more test reagents in the reaction vessel, as a result of which a biochemical reaction is started which brings about a measurable change in an optical property of the test mixture.

The measurement result is in turn forwarded by the measurement system to a storage unit and evaluated. Subsequently, the analysis apparatus supplies sample-specific measurement values to a user via an output medium, e.g. a monitor, a printer or a network connection.

The reaction vessels (cuvettes) with the reaction mixtures are often delivered to the various measurement systems on a circular transport wheel. A wheel of this kind is usually arranged with a perpendicular central shaft in the automatic analysis apparatus and has, along its outer circumference, a large number of receiving positions for reaction vessels. The reaction vessels are usually cylindrical and are oriented with their central axis parallel to that of the transport wheel. In this way, the reaction vessels can be inserted from above into the receiving positions, moved to another location by means of rotation of the transport wheel and once again removed there or filled with sample liquid or reagent liquid.

In some cases, transport wheels of this kind for reaction vessels have considerable diameters depending on the number of receiving positions. In larger analysis apparatus, a transport wheel can easily reach a diameter of 80 to 90 cm. At the same time, however, it is necessary to ensure that a high degree of positioning accuracy is maintained, in order to permit the desired automatic access by gripper arms, pipetting devices, etc. Therefore, the transport wheel is typically quite solid and designed in one piece. This has the disadvantage that production of the transport wheels is difficult and therefore also expensive.

The object of the invention is therefore to make available a device for transporting reaction vessels in an automatic analysis apparatus, which device permits a high degree of positioning accuracy and can also be produced in a particularly simple and cost-effective manner.

According to the invention, this object is achieved by the fact that the transport wheel has a circular base plate, and a plurality of circular-ring-segment-shaped holders connected releasably to the base plate.

This also has the advantage that increased flexibility of the system is achieved, since the holders with the receiving positions for the reaction vessels can be easily exchanged. For example, if another type of reaction vessel is to be used in the analysis apparatus and has different dimensions than the one previously used, it is not necessary to disassemble the entire transport wheel and replace it with a new, complexly produced transport wheel with suitable receiving positions, and instead it is simply the holders mounted on the base plate that have to be exchanged. Moreover, in the event of some of the receiving positions becoming contaminated, it is not necessary to disassemble and clean the entire transport wheel, and instead it is possible for just the holders affected by the contamination to be exchanged or removed for cleaning.

The subject of the present invention is therefore a circular device for transporting reaction vessels in an automatic analysis apparatus, said device having a large number of receiving positions for receiving in each case one reaction vessel. The device according to the invention comprises a circular base plate, and a plurality of circular-ring-segment-shaped holders connected releasably to the base plate, wherein the circular-ring-segment-shaped holders comprise the receiving positions for the reaction vessels.

The circular base plate, preferably made in one piece, ensures that the transport device has the stability necessary for the positioning accuracy. For a particularly high level of stability, the base plate is advantageously made of a metal, in particular of steel. This affords a particularly high degree of torsional stiffness, such that the positioning of the reaction vessels can take place in a particularly precise manner. This in turn ensures the correct interaction with other devices of the automatic analysis apparatus, e.g. with gripper arms or pipetting devices.

The circular-ring-segment-shaped holders with the receiving positions for the reaction vessels are connected to the base plate with a force fit, but releasably. Bolts or screw bolts, for example, are suitable for the force-fit connection of the holders to the base plate.

The circular-ring-segment-shaped holders are preferably made of plastic. This has the advantage that the holders can be produced in a simple and cost-effective manner, but also with precision, for example by injection molding. Suitable plastics for the production of the circular-ring-segment-shaped holders are, for example, polypropylene, polyethylene or polyoxymethylene, and electrically conductive plastics.

In a preferred embodiment, some or all of the circular-ring-segment-shaped holders are of identical shape. This simplifies the production process and also assembly. The circular-ring-segment-shaped holders are produced such that a predefined number completely covers the circular base plate and thus forms a closed ring of circular-ring segments on the base plate. The circular-ring-segment-shaped holders can thus be produced in large numbers in a mold by injection molding and can be secured on the base plate by simple assembly.

In an additional or alternative advantageous embodiment, a circular-ring-segment-shaped holder has receiving positions which are arranged on different radii with respect to the circular transport device, i.e. concentrically. In this way, the number of the receiving positions for reaction vessels can be increased while the wheel retains the same diameter. The receiving positions are then arranged on the respective circular-ring segment in arcs of a circle of different radius. The receiving positions are preferably arranged in at least two arcs of a circle of different radius. The arrangement in three, four, five or more arcs of a circle of different radius is likewise possible. Here, receiving positions arranged on a smaller radius are advantageously arranged higher than receiving positions arranged on a larger radius. Thus, the upper edge of the receiving positions arranged farther to the inside on the wheel is higher than the upper edge of the receiving positions arranged farther to the outside. This has the advantage that receiving positions lying toward the inside can be easily reached by gripper arms with which the reaction vessels in the receiving positions are accessed radially from the outside.

In another advantageous embodiment, the device for transporting reaction vessels according to the invention has a toothed ring for engagement in a motorized toothed wheel. The toothed ring serves to drive and control the rotation of the circular transport device for reaction vessels. A toothed wheel provided is close spatial proximity to the transport device is moved by a motor, which is in turn controlled by the control device of the automatic analysis apparatus. The transport device is moved by the movement of the toothed wheel, which engages in the toothed ring of the transport device, and the reaction vessels located in the receiving positions are positioned. Advantageously, the toothed ring is arranged on the outer circumference of the circular transport device, such that no inaccuracies in positioning are caused by oscillation or torsion as a result of the elasticity of the material, as could occur, for example, in the case of a drive in the shaft of the wheel.

In a particularly advantageous embodiment, the toothed ring is formed by the fact that the circular-ring-segment-shaped holders connected releasably to the base plate have a toothed edge. This permits simple production of the toothed ring, particularly if the holders are made of plastic and can be produced by injection molding of plastics. The toothed ring of the transport device therefore no longer has to be milled, as in the hitherto customary one-part designs. The entire device can thus be produced more cost-effectively. At the edge of the respective holder, where toothed-ring parts of different holders abut each other, these parts should each be designed such that the pitch of the toothed profile is maintained, i.e. the spaces between the teeth are also maintained across segment boundaries.

In another advantageous embodiment of the transport device according to the invention, the base plate has a peripheral knife edge which faces toward the center point and which engages in peripheral grooves of rotatably mounted cylinders. This permits rotatable bearing and fixing of the circular transport device. The number and the distribution of the cylinders are such that a stable knife-edge bearing is ensured and the wheel is fixed in all directions.

The present invention further relates to an automatic analysis apparatus with a device according to the invention for transporting reaction vessels, wherein the device is mounted rotatably.

In an advantageous embodiment, the analysis apparatus has at least one motorized toothed wheel, which is arranged such that it is suitable for engaging in the toothed ring of a transport device according to the invention for reaction vessels. The motorized toothed wheel, which engages in the toothed ring of the transport device, effects the movement of the transport device and, therefore, the positioning of the reaction vessels located in the receiving positions.

In another advantageous embodiment, the analysis apparatus has at least two rotatably mounted cylinders with peripheral grooves, wherein the rotatable cylinders are arranged so as to be suitable for engagement in a knife edge which extends around the base plate and faces toward the center point of the base plate. The number and the distribution of the cylinders are such that a stable knife-edge bearing is ensured and the wheel is fixed in all directions.

In a particularly advantageous embodiment, the analysis apparatus has three of these rotatably mounted cylinders. The latter are advantageously arranged at the corners of an isosceles triangle within the circular transport device, such that a uniform hold of the transport device is ensured in all directions. One of the cylinders is advantageously self-resetting by being pivotable in the direction of the center point of the circular transport device. This can be achieved by a suitable spring arrangement, for example. By means of the resilient bearing, the finished transport device, with its base plate and with the holders arranged thereon, is particularly easy to assemble.

The present invention further relates to a circular-ring-segment-shaped holder with a plurality of receiving positions, wherein each receiving position is provided for one reaction vessel in each case. A holder of this kind is suitable for mounting on a circular base plate and, therefore, for producing a circular device for transporting reaction vessels in an automatic analysis apparatus.

In an advantageous embodiment, the holder is made of plastic, preferably of polypropylene, polyethylene, polyoxymethylene, or of an electrically conductive plastic.

In another advantageous embodiment, the holder has a toothed edge.

The receiving positions of the holder are preferably arranged concentrically on different radii of the circular-ring segment. The receiving positions arranged on a smaller radius, i.e. lying farther to the inside, are preferably arranged higher than the receiving positions arranged on a larger radius, i.e. farther to the outside. The receiving positions are preferably arranged in at least two arcs of a circle of different radius. An arrangement in three, four, five or more arcs of a circle of different radius is likewise possible.

The advantages afforded by the invention are in particular that, since the circular base plate and the holders for receiving positions are produced separately, a wheel for transporting cuvettes is made available that is particularly stable and at the same time easy to produce. By injection molding of plastic, the production process of certain embodiments is particularly flexible, and many different kinds of requirements can be integrated, e.g. toothed rings for motorized control, and receiving positions for reaction vessels in different heights and radial arrangements.

Figure 4:
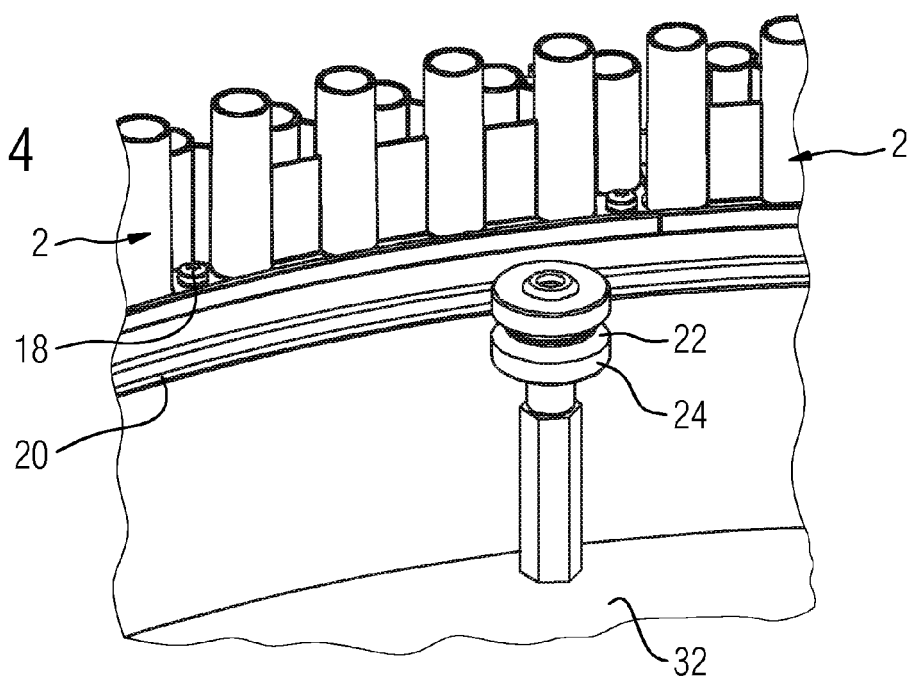
Figure 5:
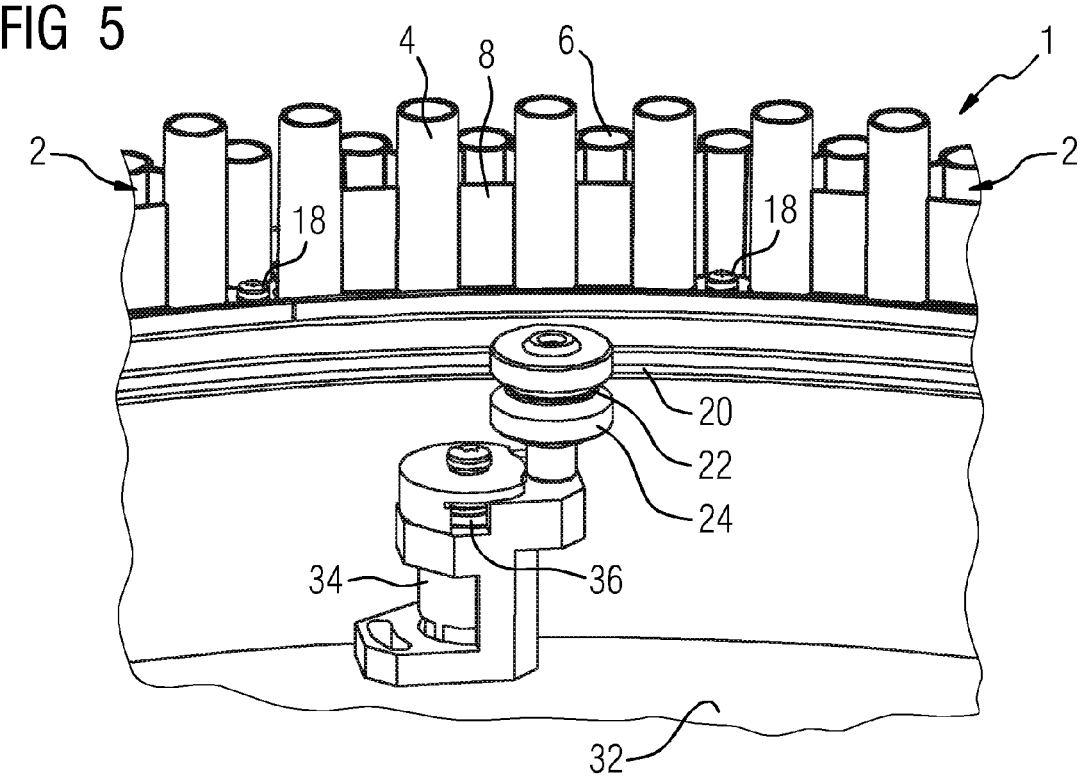
Figure 6:
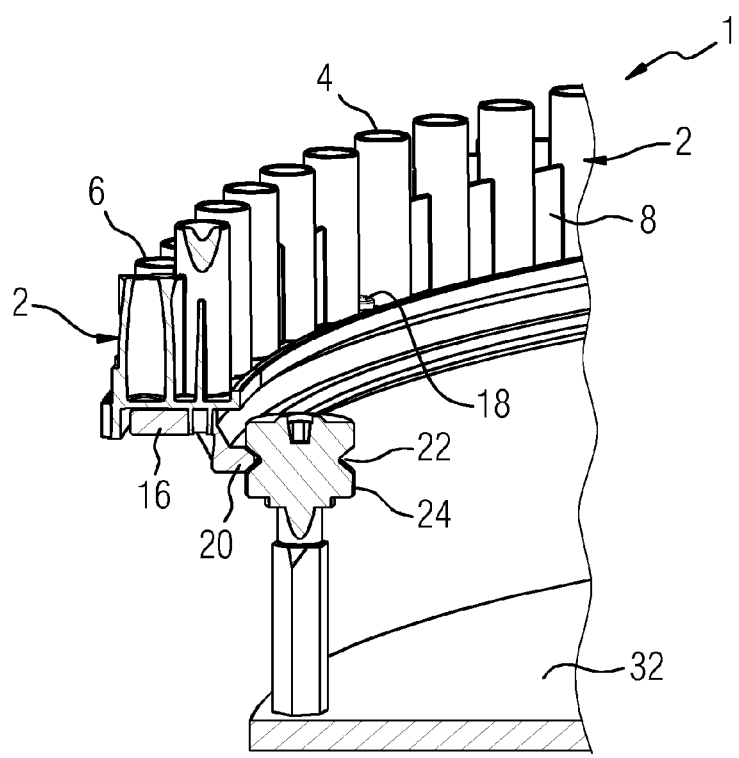
Figure 7:
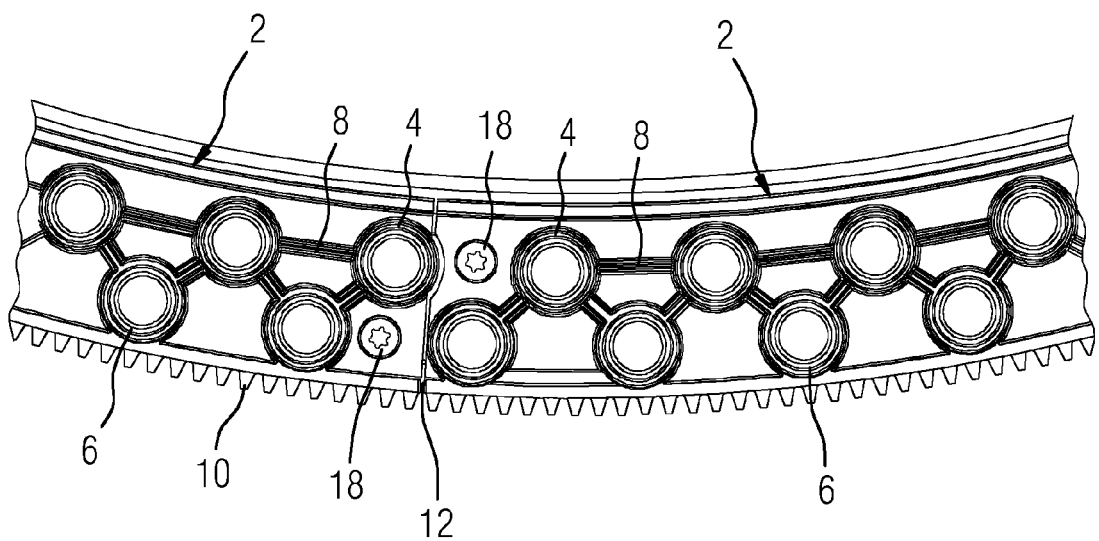

The invention is explained in more detail with reference to a drawing, in which:

FIG. 1 shows a circular-ring-segment-shaped holder made of plastic and having receiving positions for reaction vessels, FIG. 2 shows a drive unit for a transport device according to the invention, FIG. 3 shows a circular base plate for receiving the circular-ring-segment-shaped holders from FIG. 1, FIG. 4 shows a fixedly mounted rotatable cylinder as knife-edge bearing, FIG. 5 shows a spring-mounted rotatable cylinder as knife-edge bearing, FIG. 6 shows a cross section through a knife-edge bearing, FIG. 7 shows an axial view of two assembled holders from FIG. 1, and FIG. 8 shows a view of the entire transport device.

Identical parts are provided with the same reference signs in all of the figures.

FIG. 1 shows a circular-ring-segment-shaped holder 2 with receiving positions 4, 6 for reaction vessels. The holder 2 has the shape of a circular-ring segment and has a total of sixteen receiving positions 4, 6 for reaction vessels. Eight of the receivers 4 are arranged on a first arc of a circle, and the other eight receivers 6 on a second concentric arc of a circle with a larger radius, i.e. farther outward.

The receiving positions 4, 6 are designed substantially as hollow cylinders open at the top. The receiving positions 4 arranged on the arc of a circle lying farther to the inside are higher than the receiving positions 6 arranged farther to the outside, such that transport arms approaching radially from the outside can reach all of the receiving positions 4, 6 without any problem. The receiving positions 4, 6 are connected in a zigzag formation by webs 8, which increase the stability.

The holder 2 is produced from plastic by injection molding. It has cylindrical bores 11 for fixing the holder 2 on the base plate 16. The length of a holder 2 is dimensioned such that a plurality of holders 2 arranged in a row on a common radius produce a closed circle.

A toothed ring 10 is arranged on the outer radius of holder 2. The teeth of the toothed ring 10 are designed at the azimuthal border 12 in such a way that, when identical holders 2 are juxtaposed on a circle, the pitch, i.e. the distance between teeth, also remains constant across segment boundaries.

FIG. 2 shows the assembled transport device 1 with a drive 14. The holders 2 are mounted on a circular base plate 16 by means of screw bolts 18. The base plate 16 is made in one piece from steel. On its inner radius, it has a radially inwardly directed and slightly downwardly offset knife edge 20. The latter engages in a groove 22, which is formed peripherally in a rotatably mounted cylinder 24. This knife-edge bearing is explained in more detail below.

The already explained toothed ring 10 extends along the outside of the thus formed transport device 1 for transporting reaction vessels. A toothed wheel 28, which is moved via the drive 14, engages in the toothed ring 10. The drive 14 is controlled by the control unit of the automatic analysis apparatus (not shown in detail), such that the control unit thus controls the positioning of the transport device.

FIG. 3 shows the already described base plate 16 in full. The latter has a circular main shape with the downwardly offset knife edge 20. A large number of threads 30 are bored into the whole base plate 16 for the purpose of fixing the holders 2 by screw bolts 18.

FIG. 4 shows a detail of the transport device 1 from the direction of the center point. The screw bolts 18 for fixing the holders 2 on the base plate 16 are visible. A cylinder 24 for the bearing of the transport device 1 is also shown. The cylinder 24 has a groove 22, which is formed peripherally in the rotatably mounted cylinder 24. The cylinder 24 is secured rotatably on its axis on a bottom plate 32.

FIG. 5 shows a further cylinder 24 which, however, is mounted on a spring. For this purpose, the cylinder 24 is not secured directly on the bottom plate 32, but instead rotatably on a securing element 34. The securing element 34 is secured rotatably on the bottom plate 32 via a second axis, which is offset with respect to the axis of the cylinder 24 but parallel. By way of a spring 36 assigned to this axis, a force is exerted that acts outwardly in relation to the transport device 1. The movement is limited mechanically. A firm support of the transport device 1 is obtained by the resilient bearing and by means of two further fixed bearings which are described in connection with FIG. 4 and are secured in the corners of an isosceles triangle on the bottom plate 32. However, the transport device 1 can be easily removed by inward pivoting of the resilient bearing.

FIG. 6 shows a cross section through one of the bearings with the cylinder 24 and shows in particular the engagement of the knife edge 20 in the groove 22. This figure likewise illustrates the cross section of the base plate 16 with the downwardly offset knife edge 20.

FIG. 7 is a top view, axially with respect to the transport device 1, showing two adjoining holders 2. Also shown are the already described receiving positions 4, 6, with the webs 8 connecting them, the screws 18 for securing on the base plate 16, and the toothed ring 10. The constant spacing of the teeth of the toothed ring 10 across the border 12 can be clearly seen.

FIG. 8, finally, shows an assembled transport device 1 with a drive 14. The transport device 1 is supported on three bearings with cylinders 24 mounted at the corners of an isosceles triangle on the bottom plate 32.

LIST OF REFERENCE SIGNS 1 transport device
2 holder
4, 6 receiving position
8 web
10 toothed ring
11 bore
12 border
14 drive
16 base plate
18 screw bolt
20 knife edge
22 groove
24 cylinder
28 toothed wheel
30 thread
32 bottom plate
34 securing element
36 spring

The invention claimed is:

1. A circular device for transporting reaction vessels in an automatic analysis apparatus, the circular device having a plurality of receiving positions for receiving in each position one reaction vessel, the circular device comprising a rotatable circular base plate, and a plurality of circular-ring-segment-shaped holders connected releasably to the base plate, wherein the plurality of circular-ring-segment-shaped holders comprises the receiving positions and a toothed ring for engaging a motorized toothed wheel, wherein the toothed ring is formed by a toothed edge on an outer circumference of each one of the circular-ring-segment-shaped holders.

2. The device as claimed in claim 1, wherein the base plate has a peripheral knife edge which faces toward a center point of the circular device and which engages in peripheral grooves of rotatably mounted cylinders.

3. The device as claimed in claim 1, wherein the base plate is made of metal, and the circular-ring-segment-shaped holders are made of plastic.

4. The device as claimed in claim 1, wherein the circular-ring-segment-shaped holders are connected releasably to the base plate with a force fit.

5. The device as claimed in claim 1, wherein some or all of the holders are of identical shape.

6. The device as claimed in claim 1, wherein a predefined number of the circular-ring-segment-shaped holders forms a closed ring of the circular-ring-segment-shaped holders on the circular base plate.

7. The device as claimed in claim 1, wherein the receiving positions of the holders are arranged concentrically on different radii with respect to a center point of the circular device.

8. The device as claimed in claim 7, wherein the receiving positions each comprise a hollow cylinder and the hollow cylinders of receiving positions arranged on an inner radius have a height greater than the hollow cylinders of receiving positions arranged on an outer radius.

9. The device as claimed in claim 3, wherein the base plate is made of steel.

10. The device as claimed in claim 4, wherein the circular-ring-segment-shaped holders are connected releasably to the base plate with a force fit using bolts or screw bolts.

11. A transport device comprising the circular device as claimed in claim 1, wherein the circular device is mounted rotatably to a bottom plate of the transport device.

12. The transport device as claimed in claim 11, wherein the transport device has at least one motorized toothed wheel for engaging in the toothed ring of the circular device.

13. The transport device as claimed in claim 11, wherein the base plate of the circular device has a peripheral knife edge which faces toward a center point of the circular device, and wherein the transport device has at least two rotatably mounted cylinders with peripheral grooves for engagement in the peripheral knife edge.

14. The transport device as claimed in claim 13, comprising at least three rotatably mounted cylinders, wherein one of the cylinders is self-resetting by being pivotable in the direction of the center point of the circular device.

\* \* \* \* \*